United States Patent
Grant

(10) Patent No.: US 8,479,370 B2
(45) Date of Patent: Jul. 9, 2013

(54) METHOD OF PREVENTING INADVERTENT INTERCONNECTION IN MEDICAL SYSTEMS USING ADAPTER

(75) Inventor: Geoffrey P. Grant, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 168 days.

(21) Appl. No.: 13/035,346

(22) Filed: Feb. 25, 2011

(65) Prior Publication Data
US 2011/0178496 A1    Jul. 21, 2011

Related U.S. Application Data

(62) Division of application No. 11/818,299, filed on Jun. 14, 2007, now abandoned.

(51) Int. Cl.
*B21D 39/00*    (2006.01)

(52) U.S. Cl.
USPC ............ 29/525.01; 29/525.11; 604/533

(58) Field of Classification Search
USPC ............ 29/525.01, 525.11; 604/533; 285/390
See application file for complete search history.

(56) References Cited

U.S. PATENT DOCUMENTS

| | | |
|---|---|---|
| 872,001 A | 11/1907 | Massie |
| 1,742,497 A | 1/1930 | Dickinson |
| 1,862,833 A | 6/1932 | Stover |
| 2,419,453 A | 4/1947 | Kocevar |
| 2,547,889 A | 4/1951 | Richardson |
| 4,046,479 A | 9/1977 | Paley |
| 4,696,326 A | 9/1987 | Sturgis |
| 4,820,265 A | 4/1989 | DeSatnick et al. |
| 5,242,423 A | 9/1993 | Goodsir et al. |
| 5,489,275 A | 2/1996 | Thompson et al. |
| 5,501,426 A | 3/1996 | Atkinson et al. |
| 5,776,117 A | 7/1998 | Haselhorst et al. |
| 6,245,055 B1 | 6/2001 | Fulford et al. |
| 6,322,551 B1 | 11/2001 | Brugger |
| 6,585,229 B2 | 7/2003 | Cote, Sr. et al. |

(Continued)

FOREIGN PATENT DOCUMENTS

JP    2003192100 A    *    7/2003

OTHER PUBLICATIONS

Election/Restriction for U.S. Appl. No. 11/818,299 dated Mar. 30, 2010, 7 pgs.

(Continued)

*Primary Examiner* — Jermie Cozart

(57) ABSTRACT

A method of preventing inadvertent interconnection between a first medical system and a second medical system utilizes a luer fitting connector/adapter that acts as a modified-to-standard size converter piece. The adapter may complete a fluid tight medical system. The adapter may have one end having at least one non-standard sized luer fitting dimension. The non-standard end of the adapter may sealingly interconnect with a luer fitting member having a corresponding non-standard sized dimension. As a result, the adapter and luer fitting member may be directly interconnected with one another while remaining incompatible with standard sized luer fittings. Using the adapter may facilitate preventing the inadvertent direct interconnection of standard sized luer fitting members intended for different purposes, such as the delivery of a feed paste or a medication to a desired location within a patient. The adapter may be directly or indirectly interconnected with a syringe nozzle to facilitate flushing the medical system or a portion thereof.

19 Claims, 10 Drawing Sheets

U.S. PATENT DOCUMENTS

| | | |
|---|---|---|
| 6,595,964 B2 | 7/2003 | Finley et al. |
| 6,604,944 B2 | 8/2003 | Swan |
| 6,860,901 B1 | 3/2005 | Baker et al. |
| 2003/0171719 A1 | 9/2003 | Veillon, Jr. et al. |
| 2005/0242578 A1 | 11/2005 | Evans et al. |

OTHER PUBLICATIONS

First Action Interview Pilot Program PreInterview Communication for U.S. Appl. No. 11/818,299 dated May 21, 2010, 2 pgs.

First Action Interview Summary for U.S. Appl. No. 11/818,299 dated Jul. 12, 2010, 2 pgs.

Examiner Interview Summary for U.S. Appl. No. 11/818,299 dated Aug. 3, 2010, 4 pgs.

Final Rejection for U.S. Appl. No. 11/818,299 dated Nov. 24, 2010, 24 pgs.

Internation Organization for Standardization (ISO), online standards catalog, Luer fitting standard, 2 pgs.

\* cited by examiner

METHOD OF PREVENTING INADVERTENT INTERCONNECTION IN MEDICAL SYSTEMS USING ADAPTER

RELATED APPLICATION

The present application is a divisional application that claims the benefit of priority under 35 U.S.C. §121 of U.S. patent application Ser. No. 11/818,299, filed Jun. 14, 2007, now abandoned and which is hereby incorporated by reference in its entirety.

BACKGROUND OF THE INVENTION

The present invention relates generally to luer fitting connector assemblies. More particularly, the invention relates to a method and apparatus for a luer fitting connector/adapter for interconnecting luer fitting members.

Luer fitting or luer lock connections are utilized in fluid flow conduits having medical or surgical applications. Typically, a male member has a slightly tapered body and is connected in fluid communication with a female member, which has a similarly tapered bore for receiving the male member, such as those described in ISO 594/1-1986(E) and ISO 594-2:1998(E). A coupling device or locking member may be mounted upon the body of the male member. The locking member may have an internally threaded collar and operate to prevent fluid leakage between the male and female members. Another purpose of the locking member may be to maintain the connection between the male and female members. Exemplary luer fitting members are disclosed by U.S. Pat. Nos. 4,452,473, 4,735,441, 5,176,415, 5,286,067, 5,549,583, 5,611,576, 5,702,374, 6,332,633, 6,344,033, 6,402,207, 4,629,455, 5,047,021, 5,620,427, 5,651,776, and 5,984,373, and International Publication Number WO 2005/097253 A1, which are all incorporated herein by reference in their entireties.

However, typical luer fitting members may be associated with tubing or medical systems having different purposes. For instance, one system may be directed toward the delivery of feed paste to the stomach of a patient, while another system may be directed toward the intravenous delivery of medication.

Conventional luer fitting members may all be sized in accordance with an industry standard, regardless of intended use. As a result, a male luer fitting member associated with the delivery of feed paste may be inadvertently interconnected with a female luer fitting member associated with the intravenous delivery of medication, or vice versa. The inadvertent interconnection of portions of different types of systems may lead to system cross-contamination and/or erroneous medical fluid delivery.

The present invention alleviates one or more of the shortcomings described above.

BRIEF SUMMARY

The present invention provides a method and apparatus associated with a luer fitting connector/adapter. The luer fitting adapter may sealingly interconnect two luer fitting members to complete a medical system, such as a medical system associated with the delivery of feed paste or medication to a desired location within a patient. The first luer fitting member may have at least one dimension sized other than in accordance with an industry standard sizing convention for luer fittings. As a result, the first luer fitting member may be directly incompatible with standard sized luer fitting members and may not be properly interconnected with a second luer fitting member without the luer fitting adapter. Accordingly, the luer fitting adapter may facilitate alleviating the inadvertent interconnection of luer fitting members associated with different medical systems/uses. The luer fitting adapter also may facilitate a seal tight interconnection between a portion of a medical system with either a standard or a non-standard tapered syringe nozzle to permit flushing the medical system.

In one aspect, a luer fitting adapter has a first end being configured to have a first dimension and a second dimension, the first dimension being sized in accordance with a standard luer fitting sizing convention and the second dimension being sized in accordance with a non-standard luer fitting sizing convention.

In another aspect, a luer fitting adapter is configured to have a first end with a first exterior thread set and a second end with a second exterior thread set. The first end also has a non-standard sized interior tapered bore, the interior tapered bore being non-standard sized with respect to an industry sizing convention for luer fittings.

In yet another aspect, a method of interconnecting luer fitting members is described. The method includes sealingly interconnecting a first non-standard dimension of a luer fitting adapter with a second non-standard dimension of a first luer fitting member. The first and second non-standard dimensions are non-standard in the sense that the first and second non-standard dimensions are incompatible with luer fittings configured in accordance with an industry luer fitting sizing convention.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
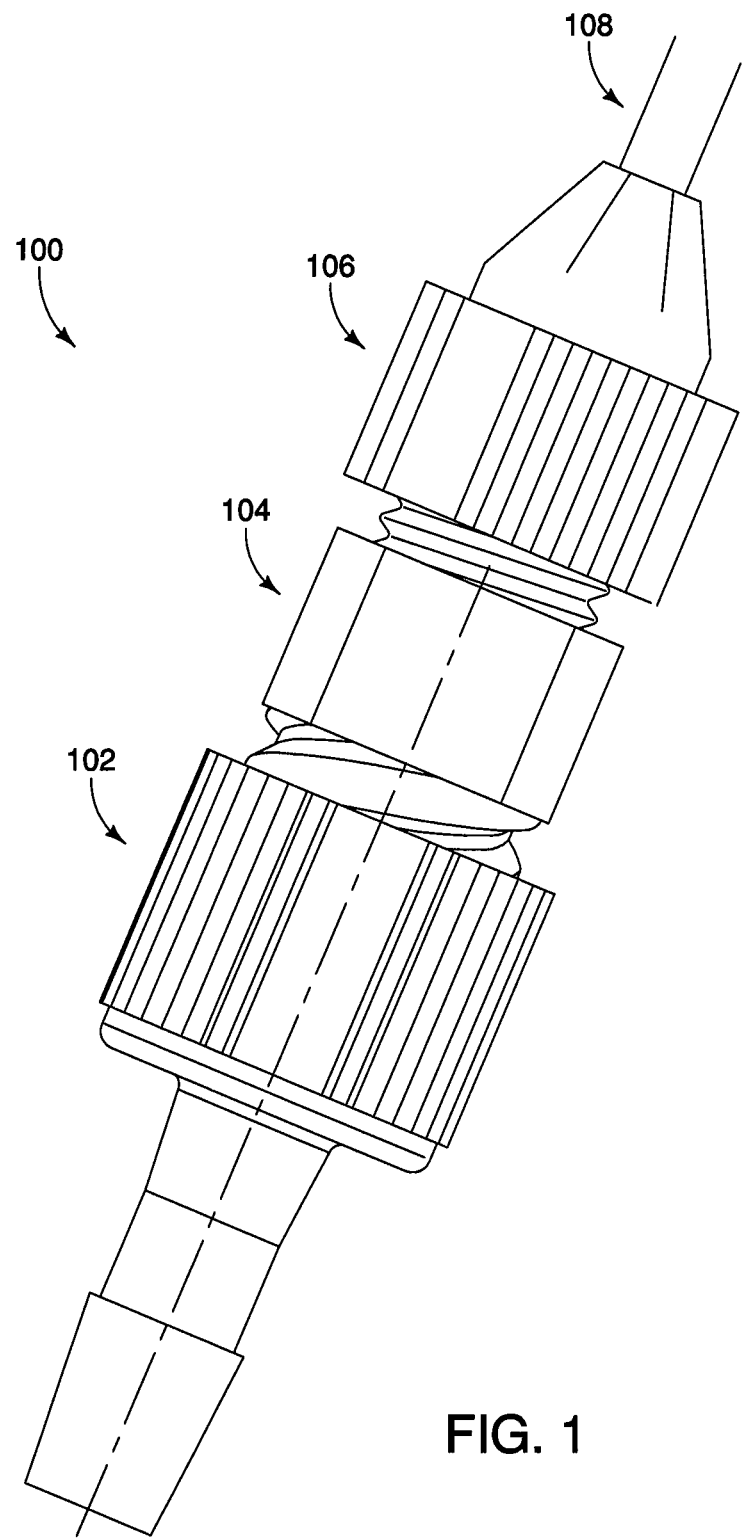
FIG. 1 is a longitudinal view of an exemplary luer fitting system of an adapter interconnected with a non-standard luer fitting and a standard luer fitting.

The method and apparatus provided may sealingly interconnect luer fitting members to complete a medical system.

The luer fitting members may be interconnected to complete various medical systems, such as medical systems associated with the delivery of feed paste to the stomach area of a patient or medication/prescribed drugs to veins or arteries, such as via intravenous (IV) lines.

Conventional luer fitting members may be sized in accordance with an industry standard, such as an ISO (International Standard Organization) or ANSI (American National Standards Institute) standard. However, configuring luer fittings associated with different types of medical systems in accordance with the same sizing convention may permit the inadvertent interconnection of those luer fittings. As one example, a male or other luer fitting member associated with the delivery of feed paste may be erroneously interconnected with a female or other luer fitting member associated with the intravenous delivery of medication. The inadvertent interconnection of luer fitting members associated with different types of medical systems may lead to system cross-contamination and/or the delivery of an inappropriate medical mixture to an area within a patient.

Accordingly, the embodiments described herein provide for distinguishing luer fitting members associated with different types of medical systems. For instance, luer fitting members associated with different types of medical systems may be configured to have differently sized inner diameters, outer diameters, lengths, thread sets, and/or other dimensions to prohibit their inadvertent interconnection.

More specifically, a first medical system may employ luer fitting members sized in accordance with an industry standard, such as the ANSI/ISO standard for luer fittings. A second medical system may employ at least one modified luer fitting member having a dimension sized in accordance with a second standard that is different than the industry standard. As a result, the luer fitting members of the first medical system and the modified luer fitting member are sized in accordance with different sizing conventions, such as being sized to have at least one different corresponding dimension such that they are directly incompatible and may not be inadvertently interconnected.

Rather than modify two luer fittings associated with the second medical system, it may be desirable to only modify a single luer fitting to be incompatible with a standard luer fittings. A luer fitting adapter may be configured to have one end operable to sealingly engage the modified luer fitting member sized in accordance with a non-standard luer sizing convention. The adapter may have a second end operable to sealing engage a standard sized luer fitting member. Therefore, the adapter may function as a modified-to-standard converter piece.

In one aspect, the modified luer fitting member may be configured to have at least one standard sized dimension and at least one non-standard sized dimension. For instance, the modified luer fitting may have a non-standard sized exterior male body tapered surface intended for sealing engagement with a corresponding interior female bore tapered surface. The female bore tapered surface may be located within one end of the adapter and sized to correspond with the non-standard sized male exterior of the modified luer fitting member.

The exterior tapered surface may have an exterior diameter or slope configured in accordance with a non-standard sizing convention. The modified luer fitting member may have a locking device having either standard or non-standard sized threads. The modified luer fitting member may have other non-standard, as well as standard, dimensions. The non-standard dimension of the modified luer fitting prevents the modified luer fitting from being inadvertently directly connected with a standard luer fitting. However, the luer fitting adapter as described herein may operate as a modified-to-standard sized converter piece that permits indirect sealing engagement between the modified and standard luer fittings sized in accordance with different sizing conventions.

In one aspect, the luer fitting adapter may directly or indirectly sealingly interconnect a feeding tube with a catheter, the feeding tube and catheter may have associated luer fitting members sized in accordance with different sizing conventions. In another aspect, the luer fitting adapter may be configured to either directly or indirectly (via a luer member) sealingly interconnect with a hard syringe to permit flushing of a medical system and/or associated tubing before, during, or after use. The flushing of the medical system may extend the life of at least a portion of the medical system, such as medical tubing connected to either a male or female (or modified or standard) luer fitting member. The flushing may involve rinsing the medical system with a high pressure fluid, such as for cleaning and sterilization purposes.

For example, a standard luer fitting member may be interconnected with a medical feed tube. A luer fitting adapter may be configured to directly or indirectly sealingly interconnect the standard luer fitting member with a either a modified luer fitting member or a non-standard sized syringe nozzle to facilitate flushing the medical tubing attached to the standard luer fitting member.

I. Exemplary Luer Fitting System

FIG. 1 illustrates a longitudinal cross-sectional view of an exemplary luer fitting system 100. The system 100 may include a non-standard or modified luer fitting member 102, a luer fitting adapter 104, a standard sized luer fitting member 106, and a medical tubing 108. The system may include additional, fewer, or alternative components.

The non-standard sized modified member 102 may have an internal fluid flow conduit. The modified member 102 may have a non-standard sized male luer fitting tapered exterior bore, for instance, the non-standard sized bore may have either a larger or smaller outer diameter than standard sized bores. The modified member 102 may have a locking device. The locking device may have a standard sized internal coarse thread set with a standard sized inner diameter. The modified member may have additional, fewer, or alternate non-standard and standard dimensions.

For instance, the modified member may have a standard sized male exterior bore and a non-standard interior thread set. The non-standard interior thread set may have either a non-standard diameter or length, or both.

The adapter 104 may have a first end and a second end. The first end may have a standard sized external thread set with a standard outer diameter. The standard sized external thread set of the first end may be a coarse thread set. As a result, the standard sized thread sets of the modified member 102 and adapter 104 may be sealingly interconnected.

The first end of the adapter 104 may have a non-standard sized interior female tapered bore. The non-standard interior tapered bore of the adapter 104 may be sized in accordance with the same non-standard sizing convention of the non-standard male portion of the modified member 102. As a result, the non-standard portions of the adapter 104 and the modified member 102 may sealingly engage for a seal tight connection.

The second end of the adapter 104 also may have a standard sized external thread set with a standard outer diameter. The standard sized external thread set of the second end may be a fine or very fine thread set, making the second end of the adapter 104 compatible with a corresponding fine interior luer fitting thread set. The standard outer diameter may be sized in accordance with an industry standard for luer fittings. The adapter may have additional, fewer, or alternate standard and non-standard dimensions.

The standard luer fitting member 106 may have a standard inner diameter and a standard sized internal thread set. The standard internal thread set may be fine or very fine. The standard dimensions of the standard luer fitting member 106 may be configured for seal tight engagement with the adapter 104, as shown in FIG. 1. The standard luer fitting member 106 may have additional, fewer, or alternate standard dimensions.

The standard luer fitting member 106 may be interconnected with a medical tubing 108. The interconnection with the medical tubing 108 may be permanent or temporary. In one aspect, the standard luer fitting member 106 may be disconnected from the medical tubing 108 during use. The medical tubing 108 may be operable to deliver feed paste or medication to a desired location.

As shown in FIG. 1, the modified member 102, the adapter 104, and the standard member 106 may all be interconnected to complete a seal tight fluid flow conduit. For instance, once interconnected, the system components may permit delivery of a feed paste from the modified member 102 to the feed tube 108.

Figure 1A:
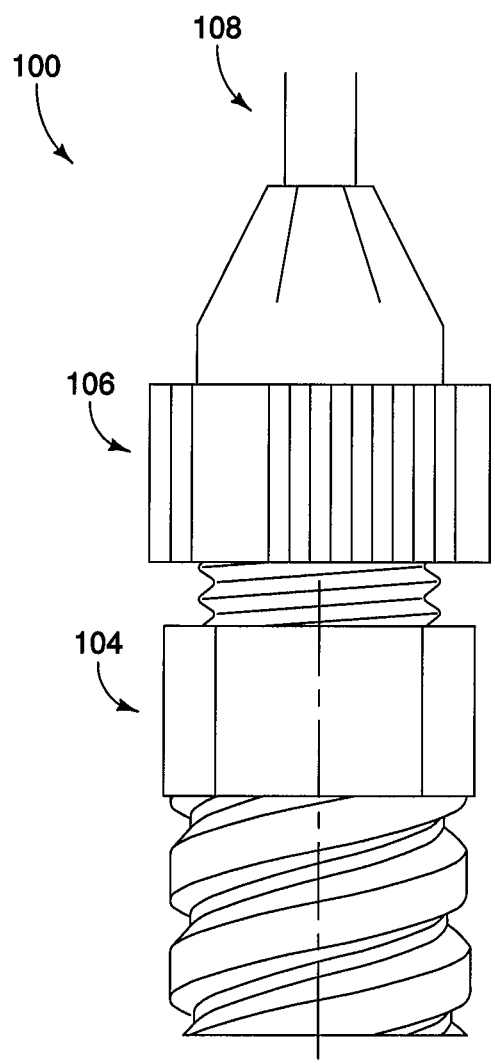
FIG. 1A is a longitudinal view of an exemplary luer fitting adapter interconnected with a standard luer fitting.

FIG. 1A illustrates a longitudinal view of the exemplary luer fitting adapter 104 interconnected with the standard luer fitting member 106 associated with a feed tube 108 of FIG. 1. As shown in FIG. 1A, the luer fitting adapter 104 has a first thread set that is coarse and a second thread set that is fine, both of which may have standard outer diameters.

II. Exemplary Modified Luer Fitting Member

Figure 2:
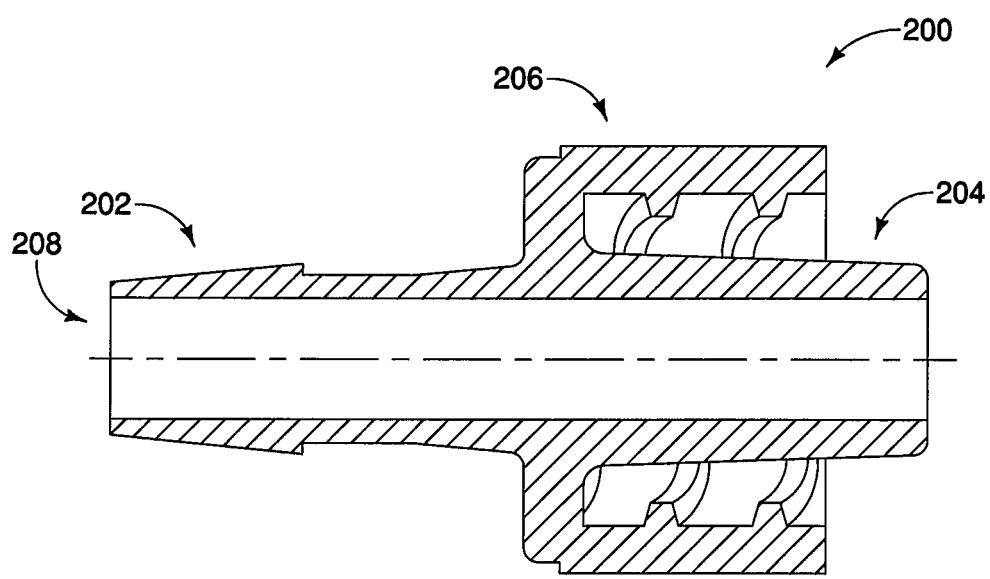
FIG. 2 is a longitudinal cross-sectional view of an exemplary modified luer fitting having a non-standard dimension.

FIG. 2 illustrates a longitudinal cross-sectional view of an exemplary modified luer fitting member 200. The modified member 200 may include a first end 202, a second end 204, a locking member 206, and a fluid flow conduit 208. In one embodiment, the modified member 200 has a longitudinal length of approximately 19.4 mm. The modified member may include additional, fewer, or alternate components.

FIG. 2 illustrates an exemplary first end 202 of the modified member 200. The exemplary first end 202 shown is configured for use with a "snap-on" luer fitting member or tube. A connecting portion of the medical system to be interconnected with the luer fitting adapter 200 may be snapped on by sliding the connecting portion over the expanding conical surface of the first end 202. Eventually, a collar or rim associated with the connecting portion may be slid over the protruding edge of the first end 202 and held in place. In one aspect, a tubular cap is snapped onto the first end 202 to prevent system fluid leakage.

As illustrated in FIG. 2, the second end 204 of the standard member 200 may be configured similar to a male luer fitting member and have a slightly tapered exterior body for insertion into and sealing engagement with a corresponding slightly tapered female bore of the luer fitting adapter. The slightly tapered exterior body of the modified member 200 may be tapered at an angle corresponding to the taper angle of the slightly tapered female bore of the adapter. The exterior surface of the slightly tapered exterior body may uniformly mate with the slightly tapered bore. The result of the union between the slightly tapered exterior body and the slightly tapered bore may be a tight seal or connection that prevents the leakage of fluid from the fluid flow conduit 208 during use.

The second end 204 may have an associated locking member 206. The locking member 206 may have an approximately circular exterior. The locking member 206 may have standard sized internal threads for locking engagement with corresponding threads or a collar on the interconnected adapter. In one embodiment, the longitudinal length of the locking member 206 is approximately 7.0 mm, the longitudinal length of the internal threaded area of the locking member 206 is approximately 5.6 mm, and the diameter of the circular exterior is approximately 9.7 mm or greater.

The standard member 200 may have a cylindrical fluid flow conduit 208. Interconnecting the second end 204 with a luer fitting adapter may complete a medical system and permit the flow of medical fluid via the fluid flow conduit 208 without leakage from one portion of the system to another. In one embodiment, the fluid flow conduit 208 may have an inner diameter of approximately 2.9 mm.

Figure 3:
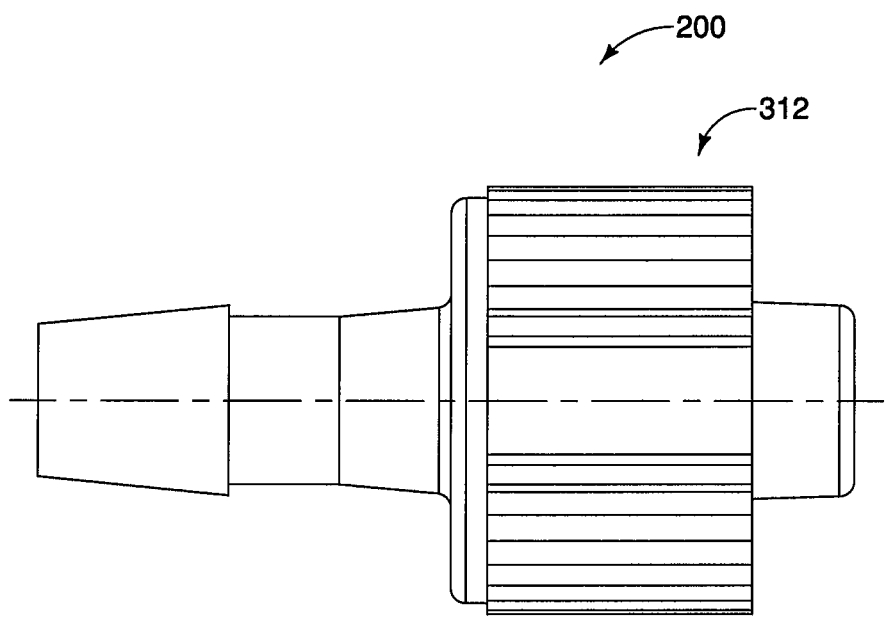
FIG. 3 is a longitudinal view of the exterior of the exemplary modified luer fitting member of FIG. 2.

FIG. 3 is a longitudinal view of the exterior of the exemplary modified luer fitting member 200 shown in FIG. 2. As shown in FIG. 3, the locking member may have grooves 312 that comprise a grip on the exterior of the standard member 200. The grooves 312 may facilitate the proper handling and operation of the standard member 200. Alternate exteriors and grips may be used.

Figure 4:
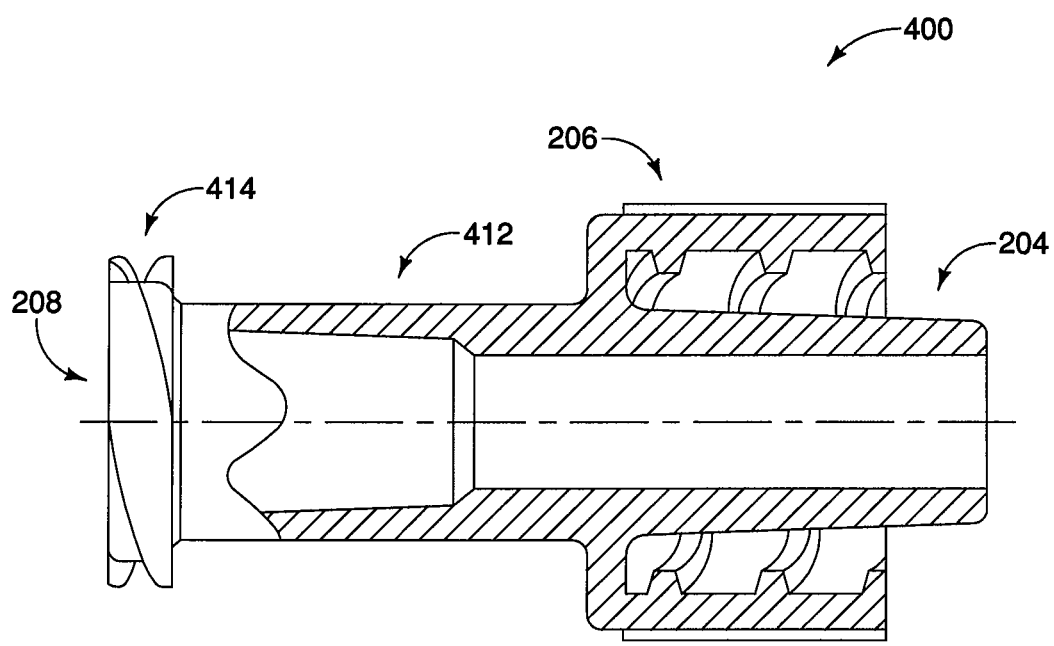
FIG. 4 is a longitudinal view of another exemplary modified luer fitting having a non-standard dimension.

FIG. 4 illustrates a longitudinal cross-sectional view of another exemplary modified member 400 having at least one non-standard sized dimension. The modified member 400 may include a first end 412, a secondary thread 414, a locking member 206, a second end 204, and a fluid flow conduit 208. In one embodiment, the modified member 400 may have a longitudinal length of approximately 20.4 mm. The modified member may include additional, fewer, or alternate components.

Again, the second end 204 of the modified member 400 may be configured to be shaped similarly to a male luer fitting member and have a slightly tapered exterior body for insertion into a tapered bore of an adapter, as discussed above with respect to FIG. 2. Conversely, the first end 412 of the modified member 400 may be configured similar to that of a female luer fitting member and have a slightly tapered bore for acceptance of and seal tight engagement with a standard sized slightly tapered exterior male body, such as a male end of a luer fitting or a male-like syringe nozzle. The surface of the tapered bore may uniformly mate with the tapered exterior body. The result of the union between the tapered exterior body and the tapered bore may be a fluid tight connection that prevents leakage from the fluid flow conduit 208. In one embodiment, a syringe nozzle or a male luer fitting member configured in accordance with the current industry standard may sealingly interconnect with the interior of the first end 412.

For example, a standard sized syringe (not shown) may be configured to be accepted by the first end 412 of the modified member 400. Alternatively, the syringe may have a nozzle with a non-standard sized tapered exterior for direct sealingly engagement with one end of the luer fitting adapter. The second end 204 of the modified member 400 may be indirectly interconnected (via an adapter and a standard member) with a catheter, a needle, other medical device, or luer fitting member. The syringe may facilitate flushing the catheter, the needle, the medical device, or medical tubing.

The modified member 400 may include an optional secondary thread 414. The secondary thread 414 may enhance the strength of the interconnection between the modified member 400 and the medical system to facilitate certain applications, such as procedures involving the delivery of medical fluids at a pressure. In one embodiment, the secondary thread 414 may have a longitudinal length of approximately 1.4 mm. Other secondary threads may be used.

III. Exemplary Luer Fitting Adapters

Figure 5:
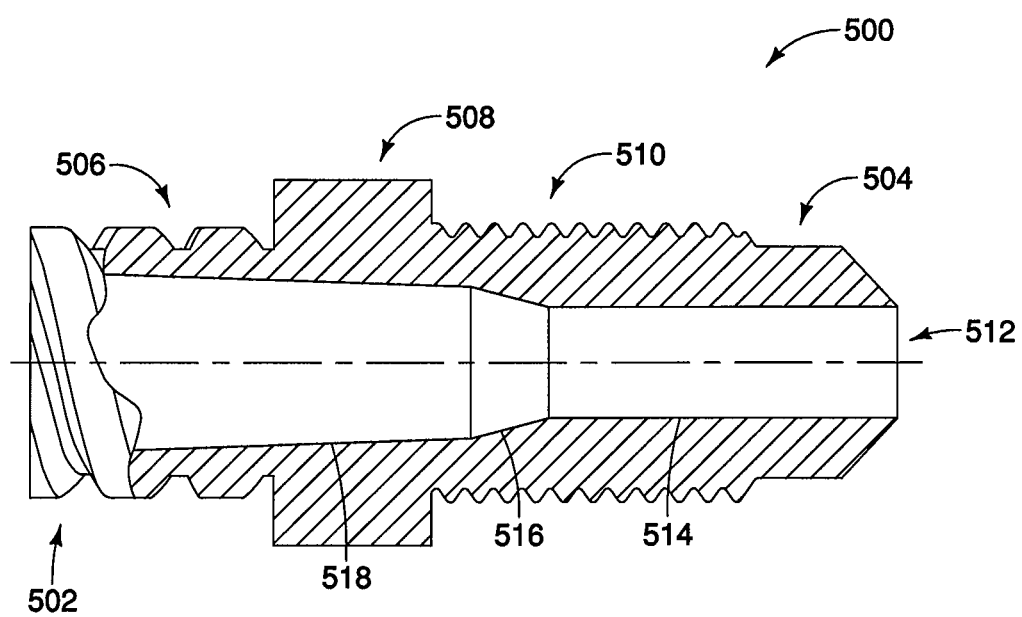
FIGS. 5 and 6 are longitudinal cross-sectional views of exemplary luer fitting adapters having at least one non-standard dimension.

FIG. 5 illustrates an exemplary luer fitting adapter 500 operable to interconnect a modified luer fitting with a standard luer fitting. The luer fitting adapter 500 may include a first end 502, a second end 504, a first thread set 506, a handle 508, a second thread set 510, and a fluid flow conduit 512. In one embodiment, the luer fitting adapter 500 may have a longitudinal length of approximately 24.3 mm. The luer fitting adapter may include additional, fewer, or alternate components.

The fluid flow conduit 512 may include a first portion 514, an expansion surface 516, and a second portion 518. The fluid flow conduit may include additional, fewer, or alternate components.

The first portion 514 may be a tubular or circular fluid flow conduit having a first uniform diameter. In one embodiment, the first uniform diameter may be approximately 3.2 mm.

The second portion 518 may be a conical fluid flow conduit having a second expanding diameter or a tapered surface. In one embodiment, the second portion 518 may have a longitudinal length of approximately 12.6 mm and a largest second diameter of approximately 5.1 mm.

The expansion surface 516 may provide for the expansion of the fluid flow conduit from the smaller first diameter to the larger second diameter. The expansion surface 516 may expand at a thirty degree or other angle. The first portion, expansion surface, and second portion may have other diameters, lengths, angles, and dimensions.

The first thread set 506 may operate to lockingly engage the luer fitting adapter 500 with a modified luer fitting member. The modified member may have a slightly tapered male portion or body for seal tight engagement with the second portion 518, as indicated by FIG. 5. In one embodiment, the first thread set 506 may have a longitudinal length of approximately 6.9 mm. The first thread set may strengthen the interconnection between the luer fitting adapter and the modified member.

As shown, the first thread set 506 may be a standard coarse thread set. The first thread set 506 may have a standard sized outer diameter. The first thread set 506 may sealingly interconnect with the standard interior thread set 206 of the modified member 200 (shown in FIG. 2). The thread sets 506, 206 may have corresponding thread sizes, such as being coarse, and corresponding outer and inner diameters. The luer fitting adapter and modified member may have other corresponding non-standard and/or standard dimensions that provide for sealingly engagement.

The second thread set 510 may operate to lockingly engage the luer fitting adapter 500 with a standard luer fitting member. The standard luer fitting member may be configured for seal tight engagement with the second end 504. In one embodiment, the second thread set 510 may have a longitudinal length of approximately 9.1 mm. The second thread set may strengthen the interconnection between the luer fitting adapter and a standard luer fitting member.

As shown, the second thread set 510 may be a standard fine thread set. The second thread set 510 may have a standard sized outer diameter. Alternatively, the second thread set 510 may have a non-standard thread set or non-standard sized outer diameter for interconnection with corresponding non-standard dimensions on the "standard" luer fitting member.

The second thread set 510 may sealingly interconnect with the thread set of the standard luer fitting member 106 (shown in FIG. 1). The thread sets may have corresponding thread sizes, such as being fine or very fine, and corresponding outer and inner diameters. The luer fitting adapter and standard member may have other corresponding standard, as well as non-standard, dimensions that provide for sealingly engagement.

The handle 508 may provide an exterior grip to enhance control and handling of the luer fitting adapter 500 during use. In one embodiment, the handle 508 may have a longitudinal length of approximately 4.4 mm. Alternate handles may be used.

Figure 6:
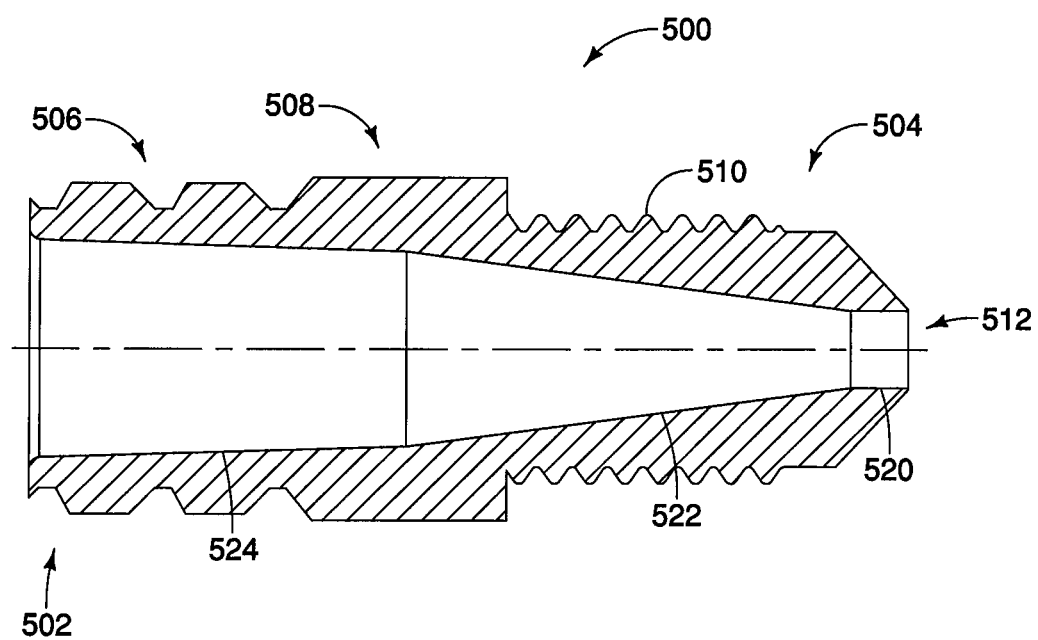

FIG. 6 illustrates another exemplary luer fitting adapter 500 operable to interconnect a modified fitting with a standard luer fitting member. The luer fitting adapter 500 may include a first end 502, a second end 504, a first thread set 506, a handle 508, a second thread set 510, and a fluid flow conduit 512. In one embodiment, the luer fitting adapter may have a longitudinal length of approximately 19.7 mm. The luer fitting adapter may include additional, fewer, or alternate components.

The outer diameter of the first end 502 may be standard sized. The first thread set 506 may be a standard thread set. The outer diameter of the second end 504 also may be standard sized. The second thread set 510 also may be a standard thread set. However, the interior tapered bore 524 of the first end 502 may be incompatible with standard male tapers and only sealingly engage with a modified male body of a modified fitting.

As a result, the luer fitting adapter may operate to sealingly interconnect a modified luer fitting member with a standard luer fitting member. In other words, the luer fitting adapter may operate as a modified-to-standard sized adapter. The luer fitting adapter may be used to adapt/convert various modified luer fitting dimensions, including exterior and interior diameters, to a standard sizing convention. Other dimensions may be adapted from a modified to a standard sizing convention.

The fluid flow conduit 512 may include a first portion 520, an expansion surface 522, and a second portion 524. The fluid flow conduit may include additional, fewer, or alternate components.

The first portion 520 may include a tubular or circular fluid flow conduit having a first uniform diameter. In one embodiment, the first portion 520 may have a longitudinal length of approximately 1.9 mm and a first uniform diameter of approximately 1.8 mm.

The second portion 524 may be a conical fluid flow conduit having a second expanding diameter or tapered surface comprising an interior tapered bore. In one embodiment, the second portion 524 may have a longitudinal length of approximately 8.4 mm and a largest interior diameter of approximately 5.1 mm.

The expansion surface 522 may provide for the expansion of the fluid flow conduit from the first to the second diameter. The expansion surface 522 may expand the fluid flow conduit 512 at an eight degree or other angle. The first portion, the second portion, and the expansion surface may have other diameters, lengths, angles, and dimensions.

Figure 7:
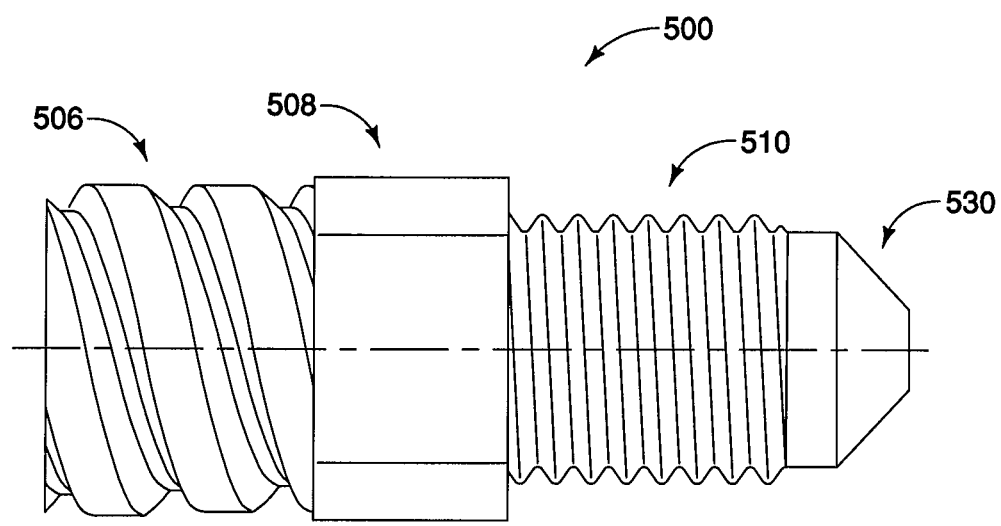
FIG. 7 is a longitudinal view of the exterior of the exemplary luer fitting adapter of FIG. 6.

FIG. 7 illustrates a longitudinal view of the exterior of the exemplary luer fitting adapter 500 of FIG. 6. As shown, the exterior of the exemplary luer fitting adapter 500 may include a first thread set 506, a handle 508, a second thread set 510, and a seal surface 530. The seal surface 530 may be configured to sealingly engage a surface on a standard luer fitting member. In one embodiment, the first thread set 506, the handle 508, the second thread set 510 may have longitudinal lengths of approximately 6.2 mm, approximately 4.5 mm, and approximately 7.4 mm, respectively. The luer fitting adapter may include additional, fewer, or alternate exterior components.

IV. Exemplary Standard Luer Fitting Member

Figure 8:
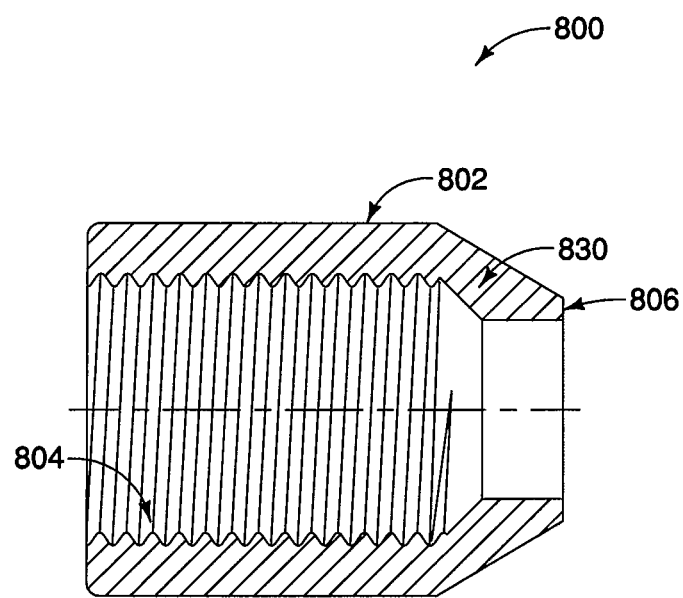
FIG. 8 is a longitudinal cross-sectional view of an exemplary standard luer fitting.

FIG. 8 illustrates a longitudinal cross-sectional view of an exemplary standard sized luer fitting member 800. The standard member 800 may include an exterior 802, internal threads 804, and a distal end 806. The standard member may include additional, fewer, or alternate components.

The internal threads 804 may be fine, very fine, and/or standard sized. The internal threads 804 may sealingly engage the second standard thread set 510 on the adapter 500. The inner diameter associated with the standard member 800 may be standard sized in accordance with a standard sizing convention. The inner diameter of the standard member 800 may correspond to the standard outer diameter of the second standard thread set 510 for seal tight engagement. The standard member and the adapter may have other corresponding standard dimensions.

In one aspect, the distal end 806 of the standard member 800 may be interconnected with a medical tube (such as the medical tube 108 shown in FIG. 1) with an internal fluid flow conduit operable to deliver a medical mixture to a desired location, such as a feed paste or medication. In one embodiment, the standard member may have a longitudinal length of approximately 14.1 mm.

In another aspect, the distal end 806 may be solid and the standard member 800 may operate as a cap used to prevent fluid leakage from one end of a luer fitting adapter interconnected at the other end with a modified luer fitting member. For instance, during use, when the adapter is interconnected with only one luer fitting member it may be desirable to affix the cap to the adapter to prevent fluid leakage.

The exterior 802 of the standard member 800 may be smooth, or have grooves, notches, or another type of grip. The exterior 802 may have a tubular shape and a uniform diameter. In one embodiment, the uniform diameter may be approximately 11.1 mm. Alternate exteriors may be used.

The standard member 800 may have one or more seal surfaces 830 configured to sealingly engage corresponding surfaces on the adapter to form seal tight systems.

V. Exemplary Method of Interconnecting Luer Fitting Members

Figure 9:
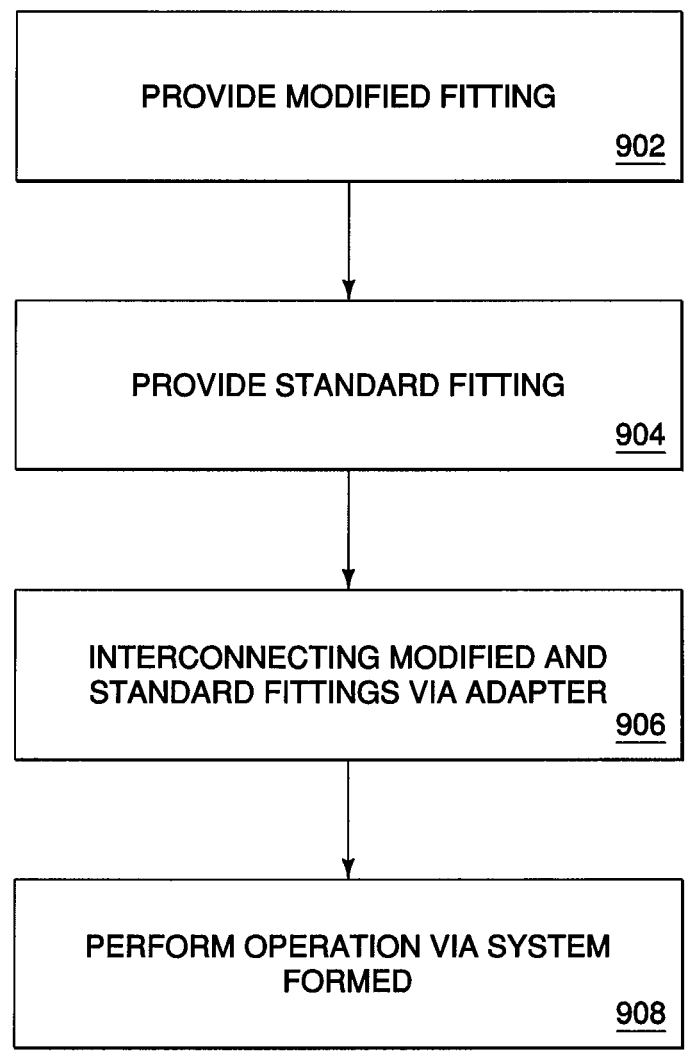
FIG. 9 is an exemplary method of interconnecting a non-standard luer fitting with a standard luer fitting via a modified-to-standard luer fitting adapter.

FIG. 9 illustrates an exemplary method of interconnecting luer fitting members. The method may include providing a first luer fitting member 902, providing a second luer fitting member 904, interconnecting the first and second members via an adapter to complete a medical system 906, and performing an operation via the system formed 908. The method may include additional, fewer, or alternate actions.

The method may include providing a first luer fitting member 902. The first luer member may be a standard male, female, or other luer fitting member, or other medical connector, such as a connector associated medical tubing or a medical device, including catheters, needles, or syringes. The first luer fitting member may have diameters, lengths, surfaces, thread sets, cavities, and/or other dimensions sized in accordance with a first standard for luer fittings, such as an industry standard. Other first luer fitting members may be provided.

The method may include providing a second luer fitting member 904. The second luer member may be a modified male, female, or other luer fitting member, or other medical connector, such as a connector associated medical tubing or a medical device, including catheters, needles, and syringes. Unlike the first luer fitting member, the second luer fitting member may be sized other than in accordance with the first (or industry) standard for luer fittings such that the first and second fittings are directly incompatible. Other second luer fitting members may be provided.

The method may include indirectly interconnecting the first and second members via a luer fitting adapter to complete a fluid tight medical system 906. The luer fitting adapter may be a modified-to-standard converter piece such that the adapter may sealingly interconnect first and second luer fittings configured in accordance with different sizing standards. Without the adapter piece, two distinct portions of the medical system associated with the first and second luer fittings, respectively, may not be interconnected.

Either the first or the second luer fitting member, or both, may belong to a specific type of medical system and may be distinguished from luer fittings associated with different types of systems, as discussed herein. For instance, the first and second luer fittings, as well as the adapter, may be physically, aurally, and/or visually distinguished from luer fittings associated with other types of medical systems to prevent inadvertent cross contamination of the systems. The physical distinction of the luer fittings and/or adapter may include the fore-mentioned different sizing conventions for one or more dimensions. Alternatively, the physical distinction may involve altering the touch and feel of the exterior of luer fittings and/or adapter associated with one system from other luer fittings as discussed further below. Other distinctions may be made between luer fittings associated with different systems.

The method may include performing an operation via the completed medical system 908. For instance, the completion of the medical system by interconnecting two portions of the system, such as two pieces of medical tubing or one piece of tubing with a medical device, may permit the delivery of a medical fluid to a desired location within the patient. The medical fluid may be a feed paste or a medication. Alternatively, the first or second luer fitting may be a hard syringe, or interconnected with a hard syringe, that facilitates flushing of the medical system, such as with pressurized water to cleanse the system. Other medical systems may be used.

Instead of or in addition to manufacturing physical incompatibilities between potential interconnecting members, luer fitting members associated with different types of medical systems may be distinguished in other manners, such as visually, aurally, or by feel. For instance, luer fitting members associated with different types of systems may be color coded. A color scheme may be selected and employed to distinguish the different types of medical systems. In one embodiment, a system associated with the intravenous delivery of a medical mixture may include a standard member, an adapter, and a non-standard member all colored white, and another system associated with the delivery of a feed paste may include a standard member, an adapter, and a non-standard member all colored red. Other color schemes may be used.

Luer fitting members associated with different types of medical systems may be distinguished aurally during operation. Luer fitting members may have one or more associated rotary or other locking devices. As a locking device/member is tightened/fastened onto a standard member, an adapter, or a non-standard member, an audible sound may be generated. Different sounds may be produced depending upon the type of medical system associated with the locking device and/or corresponding members and adapter.

A medical system associated with the intravenous delivery of a medical mixture may include a locking device operable to generate a "clicking" sound as the locking device is turned with respect to a standard member, an adapter, or a non-standard member. On the other hand, a second medical system associated with the delivery of feed paste may include a locking device operable to generate a different type of sound or no sound at all as the locking device is turned with respect to one of the pieces. Alternatively, the second medical system may have a "snap on" locking device instead of a rotary locking device, which also may generate a unique sound during use. As a result, during operation, if an operator hears an unexpected audible sound, or does not hear an expected audible sound, when interconnecting the pieces via the locking device, the operator may be alerted that the pieces are associated with different types of medical systems and not intended to be interconnected.

Luer fitting members associated with different types of medical systems may be distinguished by touch or feel. Luer fitting members may have associated exterior grips, grooves, notches, or other exteriors. Standard and non-standard members (such as a standard male and a non-standard female fitting members) associated with a specific medical system may have similar exteriors. If an operator inadvertently grabs two luer fitting members associated with different types of medical systems and having different exteriors, the operator may be alerted that the two luer fitting members belong to different systems and are not intended to be interconnected. Other manners of distinguishing luer fitting members associated with different medical systems may be used.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

The invention claimed is:

1. A method of preventing inadvertent interconnection between a first medical system and a second medical system, the method comprising:
    selecting a luer fitting adapter for use in the first medical system having a first luer connector that is incompatible with a second luer connector in the second medical system, the adapter having a first end comprising (i) a locking member having a first dimension, and (ii) a luer connector means to prevent inadvertent interconnection between the first luer connector and the second luer connector, the luer connector means comprising one of a male luer fitting member and a female luer fitting member of the first luer connector having a second dimension that is incompatible with the second luer connector and wherein the adapter has a second end having a surface adapted to sealingly engage with a second component of the first medical system;
    connecting the adapter in the first medical system;
    connecting the second component to the second end of the adapter; and
    delivering one of a medicine and a feed paste via the first medical system:
    wherein each of the first luer connector and the second luer connector includes a male luer fitting member having a tapered body and an associated female luer fitting member having a similarly tapered bore for receiving and connecting with the associated male luer fitting member in fluid communication.

2. The method of claim 1, wherein the second dimension is an inner diameter for the luer fitting member.

3. The method of claim 2, wherein the first dimension is a dimension of a thread set and the second dimension is a tapered bore of a female luer fitting member adapted to sealingly engage a correspondingly sized exterior taper of the male luer fitting member of the first luer connector.

4. The method of claim 3, wherein the male luer fitting member is a nozzle of a syringe.

5. The method of claim 1, wherein the first end has a coarse external thread set adapted to interconnect with a corresponding coarse internal thread set of a first component of the first medical system, the adapter further having a second end having a fine external thread set adapted to interconnect with a corresponding fine internal thread set of a second component of the first medical system.

6. The method of claim 5, wherein the second component of the first medical system comprises a feeding tube for delivering feed paste to a desired location.

7. A method of preventing inadvertent interconnection between a first medical system and a second medical system, the method comprising:
    selecting a luer fitting adapter for use in the first medical system having a first luer connector that is incompatible with a second luer connector in the second medical system, the adapter comprising a first end with a first exterior thread set and a second end with a second exterior thread set, wherein the first end has a luer connector means to prevent inadvertent interconnection between the first luer connector and the second luer connector, the luer connector means comprising an interior tapered bore that is incompatible with the second luer connector;
    connecting the adapter in the first medical system; and
    delivering one of a medicine and a feed paste via the first medical system:
    wherein each of the first luer connector and the second luer connector includes a male luer fitting member having a tapered body and an associated female luer fitting member having a similarly tapered bore for receiving and connecting with the associated male luer fitting member in fluid communication.

8. The method of claim 7, wherein the first and second ends have outer diameters that are compatible with the second luer connector.

9. The method of claim 7, wherein the interior tapered bore is adapted to sealingly engage a correspondingly sized exterior tapered body of a male luer fitting member of the first luer connector.

10. The method of claim 9, wherein the first exterior thread set is adapted to interconnect with a corresponding interior thread set of a first component of the first medical system.

11. The method of claim 9, wherein the first component comprises a catheter.

12. The method of claim 7, wherein the adapter is adapted to interconnect with a second component of the first medical system, the second component comprising a feeding tube for delivering feed paste to a desired location.

13. A method of interconnecting luer fitting members comprising a male luer fitting member having a tapered body and a female luer fitting member having a tapered bore for receiving and connecting in fluid communication with a male luer fitting member, the method comprising:
    sealingly interconnecting a first non-standard dimension of a luer fitting adapter with a second non-standard dimension of a first luer fitting member, the first and second non-standard dimensions being non-standard in the sense that the first and second non-standard dimensions are incompatible with luer fittings configured in accordance with an industry luer fitting sizing convention, and wherein the first non-standard dimension corresponds to a non-standard sized interior tapered bore of the adapter and the second non-standard dimension corresponds to a non-standard sized exterior tapered body of the first luer fitting member;

sealingly interconnecting the adapter with a second luer fitting member, the adapter having a first standard sized dimension that corresponds to a second standard sized dimension of the second luer fitting member; and delivering one of a medicine and a feed paste to a desired location via a system formed by the interconnection of the adapter with the first and second luer fitting members.

14. The method of claim 13, the method comprising flushing a medical tube associated with the second luer fitting member.

15. The method of claim 14, the method comprising physically distinguishing at least one of the first and the second luer fitting members from luer fittings associated with a different type of medical system.

16. A method of preventing inadvertent interconnection between a first luer connector in a luer fitting connector assembly, and a second luer connector in a second medical system, the method comprising:

selecting a luer fitting member having a proximal end and a distal end, the proximal end including an opening having an inner diameter and a first internal thread set, and the distal end having an opening in fluid communication with the proximal opening and being interconnected with a medical tubing having an internal fluid flow conduit for delivery of a medical mixture to a desired location;

selecting a luer fitting adapter having a first end with a first exterior thread set and a second end with a second exterior thread set, the second exterior thread set being sized to threadingly mate with the first internal thread set of the luer fitting member, and the first end including a luer connector means to prevent inadvertent interconnection between the first luer connector of the luer fitting connector assembly and the second luer connector, the luer connector means comprising an interior tapered bore that is incompatible with the second luer connector;

connecting the adapter to the luer fitting member;

selecting a modified luer fitting member having (i) a male luer fitting sized to mate with the interior tapered bore of the luer fitting adapter, and (ii) a locking member having an internal thread set sized to threadingly mate with the first exterior thread set of the first end of the luer fitting adapter; and connecting the luer fitting member to the luer fitting adapter.

17. The method of claim 16, wherein the medical mixture to be delivered by the medical tubing is one of a feed paste and a medication.

18. The method of claim 16, wherein the luer fitting member includes a seal surface to sealingly engage a corresponding surface on the luer fitting adapter to form a fluid tight seal.

19. The method of claim 16, wherein the first exterior thread set and the second exterior thread set have different dimensions.

* * * * *

UNITED STATES PATENT AND TRADEMARK OFFICE
CERTIFICATE OF CORRECTION

PATENT NO. : 8,479,370 B2  
APPLICATION NO. : 13/035346  
DATED : July 9, 2013  
INVENTOR(S) : Geoffrey P. Grant Page 1 of 1

It is certified that error appears in the above-identified patent and that said Letters Patent is hereby corrected as shown below:

In the Claims

In column 13, claim 15, line 12, replace "The method of claim 14," with --The method of claim 13,--.

Signed and Sealed this  
Tenth Day of September, 2013

Teresa Stanek Rea  
*Acting Director of the United States Patent and Trademark Office*